(12) United States Patent
Warnock (10) Patent No.: US 10,390,903 B2
(45) Date of Patent: Aug. 27, 2019

(54) ILLUMINATED APPARATUS WITH TELESCOPING FOR ELECTROCAUTERY DEVICES AND METHOD OF USE

(71) Applicant: Steven Warnock, Salt Lake City, UT (US)

(72) Inventor: Steven Warnock, Salt Lake City, UT (US)

(*) Notice: Subject to any disclaimer, the term of this patent is extended or adjusted under 35 U.S.C. 154(b) by 49 days.

(21) Appl. No.: 15/332,427

(22) Filed: Oct. 24, 2016

(65) Prior Publication Data
US 2018/0110582 A1  Apr. 26, 2018

(51) Int. Cl.
*A61B 90/30* (2016.01)
*A61B 18/08* (2006.01)
*A61B 17/00* (2006.01)

(52) U.S. Cl.
CPC ............ *A61B 90/30* (2016.02); *A61B 18/082* (2013.01); *A61B 2017/00734* (2013.01); *A61B 2017/00991* (2013.01); *A61B 2090/304* (2016.02); *A61B 2090/309* (2016.02); *A61B 2218/008* (2013.01)

(58) Field of Classification Search
CPC ....... A61B 1/06; A61B 1/0607; A61B 1/0615; A61B 1/0623; A61B 1/063; A61B 1/0676; A61B 1/0684; A61B 1/0692; A61B 2018/00571–0063; A61B 2018/2255
See application file for complete search history.

(56) References Cited

U.S. PATENT DOCUMENTS

| | | | |
|---|---|---|---|
| 1,570,623 A | 1/1926 | De Zeng | |
| 1,608,726 A | 11/1926 | De Zeng | |
| 2,229,310 A | 1/1941 | Saslaw | |
| 4,688,569 A | 8/1987 | Rabinowitz | |
| 4,919,129 A * | 4/1990 | Weber, Jr. | A61B 18/1402 604/35 |
| 5,413,575 A * | 5/1995 | Haenggi | A61B 18/1402 606/39 |
| 5,693,044 A * | 12/1997 | Cosmescu | A61B 18/042 604/35 |
| 6,146,353 A * | 11/2000 | Platt, Jr. | A61B 18/00 604/22 |
| 6,458,125 B1 | 10/2002 | Cosmescu | |
| 6,562,032 B1 | 5/2003 | Ellman | |
| 7,112,199 B2 | 9/2006 | Cosmescu | |

(Continued)

FOREIGN PATENT DOCUMENTS

WO  WO 2017031245  2/2017

OTHER PUBLICATIONS

"International Search Report and Written Opinion of the International Searching Authority", from related PCT App 2017/57061, dated Jan. 12, 2018.

*Primary Examiner* — Lynnsy M Summitt
(74) *Attorney, Agent, or Firm* — Durham Jones & Pinegar; Sarah W. Matthews; Randall B. Bateman (57) ABSTRACT

An illumination device for use with a standard electrocautery pencil is described, having a distal end capable of telescoping for use with cautery extenders. The illumination device also has a light source on the distal end to reduce shadow problems, and a tube is provided for evacuation of smoke from the surgical field. The device is sized to fit on any standard electrocautery pencil. The light-emitting component on the device reduces shadows and evacuates smoke from the treatment sight without necessitating purchase of a new electrocautery device.

20 Claims, 5 Drawing Sheets

(56) References Cited

U.S. PATENT DOCUMENTS

| | | |
|---|---|---|
| 7,156,842 B2 | 1/2007 | Sartor et al. |
| 7,156,844 B2 | 1/2007 | Reschke et al. |
| 7,503,917 B2 | 3/2009 | Sartor et al. |
| 7,879,033 B2 | 2/2011 | Sartor et al. |
| 7,959,633 B2 | 6/2011 | Sartor et al. |
| 8,235,987 B2 | 8/2012 | Craig |
| 8,449,540 B2 | 5/2013 | Sartor et al. |
| 8,690,872 B2 | 4/2014 | Jayaraj |
| 9,510,737 B2 * | 12/2016 | Vayser ............... A61B 1/015 |
| 2005/0113823 A1 | 5/2005 | Reschke et al. |
| 2005/0113824 A1 | 5/2005 | Sartor et al. |
| 2006/0041257 A1 | 2/2006 | Sartor et al. |
| 2006/0178667 A1 | 8/2006 | Sartor et al. |
| 2006/0189849 A1 | 8/2006 | Sharratt et al. |
| 2006/0282072 A1 | 12/2006 | DeRosier |
| 2007/0049927 A1 | 3/2007 | Saltzman |
| 2007/0093810 A1 | 4/2007 | Sartor et al. |
| 2008/0147058 A1 | 6/2008 | Horrell et al. |
| 2009/0143778 A1 | 6/2009 | Sartor et al. |
| 2009/0149851 A1 | 6/2009 | Craig |
| 2010/0030033 A1 | 2/2010 | Farley et al. |
| 2010/0125172 A1 | 5/2010 | Jayaraj |
| 2010/0198009 A1 * | 8/2010 | Farr ............... A61B 1/00103 600/109 |
| 2011/0006033 A1 | 3/2011 | Cheng |
| 2011/0060332 A1 * | 3/2011 | Cheng ............... A61B 1/0684 606/42 |
| 2011/0092971 A1 | 4/2011 | Sartor et al. |
| 2011/0112530 A1 | 5/2011 | Keller |
| 2012/0283728 A1 * | 11/2012 | Cosmescu ............ A61B 90/35 606/46 |
| 2012/0303024 A1 | 11/2012 | Craig |
| 2013/0197317 A1 | 8/2013 | Daniel et al. |
| 2013/0267787 A1 | 10/2013 | Warnock |
| 2014/0081086 A1 * | 3/2014 | Shvetsov ........... A61B 18/1402 600/249 |
| 2014/0155701 A1 | 6/2014 | Jayaraj |
| 2014/0276797 A1 | 9/2014 | Batchelor et al. |
| 2014/0276799 A1 | 9/2014 | Batchelor et al. |
| 2014/0276800 A1 | 9/2014 | Batchelor et al. |
| 2014/0293590 A1 | 10/2014 | Pathy |
| 2016/0038017 A1 * | 2/2016 | Robinson ........... A61B 1/00071 600/104 |
| 2016/0157920 A1 * | 6/2016 | Vayser ............ A61B 18/1402 600/249 |

\* cited by examiner

ILLUMINATED APPARATUS WITH TELESCOPING FOR ELECTROCAUTERY DEVICES AND METHOD OF USE

BACKGROUND OF THE INVENTION

1. The Field of the Invention

The present invention relates to surgical tools. More specifically, the present invention relates to an illumination apparatus for use on an electrocautery or electrosurgical device.

2. State of the Art

Surgery generally involves cutting, repairing and/or removing tissue or other materials from a body, whether human or animal. These applications are generally performed by cutting tissue, fusing tissue, or tissue destruction. One of the most ubiquitous procedures to perform these functions in surgery is electrocautery. Many surgeons use electrocautery or electrosurgery instruments because their use is typically cleaner, safer, and more efficient than many of the alternatives.

"Electrocautery" or "electrosurgery" devices as used broadly herein are designed to coagulate and seal blood vessels, or incise, cut or destroy tissue with heat emanating from the device, or they perform the same functions by creating heat in the tissue via electrical current passing out of the device. For convenience, either modality is referred to herein collectively as electrocautery unless specified as being one or the other. Depending on the voltage used or the heat applied in electrocautery, the instrument can have varying effects on the patient's body, such as cutting through soft tissue to access a surgical site, or sealing off blood vessels during surgery to keep the site clean and reduce blood loss. Electrocautery may also be used in ablation or removal of undesirable tissue.

An electrocautery device uses a very high frequency, usually upwards of 100 kHz, to minimize the effect of electrical current on nerves and muscles. The voltage for the electrocautery device is generated by an electrosurgical generator or electrosurgical unit (ESU). Likewise, an ESU can produce a high frequency which is converted into heat by a resistive element or a ferromagnetic material to heat an electrocautery device. The ESU is connected to the instrument, such as an electrocautery pencil, which is held by the surgeon. The electrocautery pencil has a handle portion and an exposed blade portion, or electrode, extending from the end. While the electrode, etc., may be blade shaped, it may also be other shapes as well. The active projection of the electrocautery device with which the surgeon "cuts" and causes hemostasis will be discussed generally as an electrode regardless of shape and regardless of whether it functions thermally or electrosurgically.

Most electrocautery pencils are disposable, and the electrode cautery tip is generally interchangeable to allow for adaptation to the specific needs of the surgeon and the procedure. Other types of electrocautery pencils may be entirely disposable.

Despite its advantages and common use, one of the persistent challenges of working with an electrocautery pencil is seeing in the depth of a dark wound. Surgical overhead lights, lighted retractors, or lights worn on the surgeon's head are often used, but these lights are not ideal as they can be cumbersome and a shadow may be cast by the surgeon's hand or by the electrocautery device itself and obscure the surgical field.

Some publications show use of an LED light on the body of the pencil; some have powered the lights through batteries; however, none have fully resolved the intricacies of where to place the light and how to proceed without necessitating entire replacement of an electrocautery pencil.

Thus there is a need for an improved device and method for illumination of the surgical field during electrocautery procedures. The improved device and method should provide a light source very close to the field, thus eliminating shadow problems. Additionally, the device and method should be simple and inexpensive to manufacture, making wide distribution easy and keeping costs down.

SUMMARY OF THE INVENTION

Described herein is an illumination device for use with an electrocautery pencil. According to one implementation of the present disclosure, a device configured to fit on a standard electrocautery pencil is provided, the device having a light source disposed at the tip. The light source may be, for example, generally circular to reduce shadow problems and improve the field view of the surgeon.

According to another implementation of the present disclosure, the light device provided could be used with any standard electrocautery pencil or electrosurgical generator, making wide distribution simple and less expensive than replacing the entire electrocautery pencil or electrosurgical generator.

According to another implementation of the present disclosure, the device may have a hole therethrough for a standard electrocautery electrode mounting end to extend through. Thus, a surgeon may slide the mounting end of an electrocautery pencil through the device with the light source.

According to another implementation of the present disclosure, the light source may be located on a sleeve configured to be attached to the end of a standard electrocautery pencil. The light source may be powered by a battery, and may be located directly on the sleeve, or connected to the sleeve via flexible positioning wires. The light source may also be powered by other suitable means.

According to another implementation, the mount or sleeve may have telescoping abilities for use with an electrocautery extender. Thus, when an extender is used, the distal end of the device with the light source may telescope outwardly to reduce shadow problems and improve the view of the surgical field.

According to another aspect, the device may be provided with a suction tube to evacuate smoke, etc. from the surgical field. The device may have a connector on the proximal end for connection to standard evacuation tubing.

These and other implementations of the present disclosure are realized in an electrocautery electrode with a light source as shown and described in the following figures and related description.

BRIEF DESCRIPTION OF THE DRAWINGS

Various embodiments of the present disclosure are shown and described in reference to the numbered drawings wherein.

It will be appreciated that the drawings are illustrative and not limiting of the scope of the invention which is defined by the appended claims. The embodiments shown accomplish various implementations and objects of the invention. It is appreciated that it is not possible to clearly show each element and implementation of the invention in a single figure, and as such, multiple figures are presented to separately illustrate the various details of the invention in greater clarity. Similarly, not every embodiment need accomplish all advantages of the present invention.

DETAILED DESCRIPTION

The following description includes various representative embodiments and specific details in order to provide a thorough understanding of the present disclosure. The skilled artisan will understand, however, that the methods and devices described below can be practiced without employing these specific details, or that they can be used for purposes other than those described herein. Indeed, they can be modified and can be used in conjunction with products and techniques known to those of skill in the art in light of the present disclosure.

Reference in the specification to "one implementation" or "an implementation" means that a particular feature, structure, or characteristic described in connection with the implementation is included in at least one implementation and not that any particular implementation is required to has a particular feature, structure or characteristic described herein. The appearances of the phrase "in one implementation" in various places in the specification are not necessarily all referring to the same implementation, and may not necessarily limit the inclusion of a particular element of the invention to a single implementation, rather the element may be included in other or all implementations discussed herein. Thus it will be appreciated that the claims are not intended to be limited by the representative implementations shown herein. Rather, the various representative implementations are simply provided to help one of ordinary skill in the art to practice the inventive concepts claimed herein.

The invention and accompanying drawings will now be discussed in reference to the numerals provided therein so as to enable one skilled in the art to practice the present invention. The drawings and descriptions are intended to be exemplary of various implementations of the invention and are not intended to narrow the scope of the appended claims. Furthermore, it will be appreciated that the drawings may show implementations of the invention in isolation and the elements in one figure may be used in conjunction with elements shown in other figures.

Furthermore, the described features, structures, or characteristics of implementations of the invention may be combined in any suitable manner in one or more implementations. In the following description, numerous specific details are provided, such as examples of products or manufacturing techniques that may be used, to provide a thorough understanding of implementations of the invention. One skilled in the relevant art will recognize, however, that implementations of the invention may be practiced without one or more of the specific details, or with other methods, components, materials, and so forth. In other instances, well-known structures, materials, or operations are not shown or described in detail to avoid obscuring implementations of the invention.

Prior to discussing particular implementations, it should be understood that the present invention is not limited to any particular structures, process steps, or materials discussed or disclosed herein, but is extended to include equivalents thereof as would be recognized by those of ordinary skill in the relevant art. More specifically, the invention is defined by the terms set forth in the claims. It should also be understood that terminology contained herein is used for the purpose of describing particular implementations of the invention only and is not intended to limit the invention to the implementations or implementations shown unless expressly indicated as such. Likewise, the discussion of any particular implementation of the invention is not to be understood as a requirement that such implementation is required to be present apart from an express inclusion of the implementation in the claims.

It should also be noted that, as used in this specification and the appended claims, singular forms such as "a," "an," and "the" may include the plural unless the context clearly dictates otherwise. Thus, for example, reference to "a spring" may include one or more of such springs, and reference to "the layer" may include reference to one or more of such layers.

As used herein, the term "substantially" refers to the complete or nearly complete extent or degree of an action, characteristic, property, state, structure, item, or result to function as indicated. For example, an object that is "substantially" enclosed would mean that the object is either completely enclosed or nearly completely enclosed. The exact allowable degree of deviation from absolute completeness may in some cases depend on the specific context, such that enclosing the nearly all of the length of a lumen would be substantially enclosed, even if the distal end of the structure enclosing the lumen had a slit or channel formed along a portion thereof. The use of "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

As used herein, the term "about" is used to provide flexibility to a numerical range endpoint by providing that a given value may be "a little above" or "a little below" the endpoint while still accomplishing the function associated with the range.

As used herein, a plurality of items, structural elements, compositional elements, and/or materials may be presented in a common list for convenience. However, these lists should be construed as though each member of the list is individually identified as a separate and unique member.

Concentrations, amounts, proportions and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

"Light source" means any source of light. A single light bulb, or multiple light bulbs working together to light an area can be a "light source." Any type of light source may be used, such as LEDs, fluorescent, incandescent, compact fluorescent, halogen, etc. Light bulbs are not necessary, and other types of light sources may be used, such as strip lighting, etc.

Figure 1:
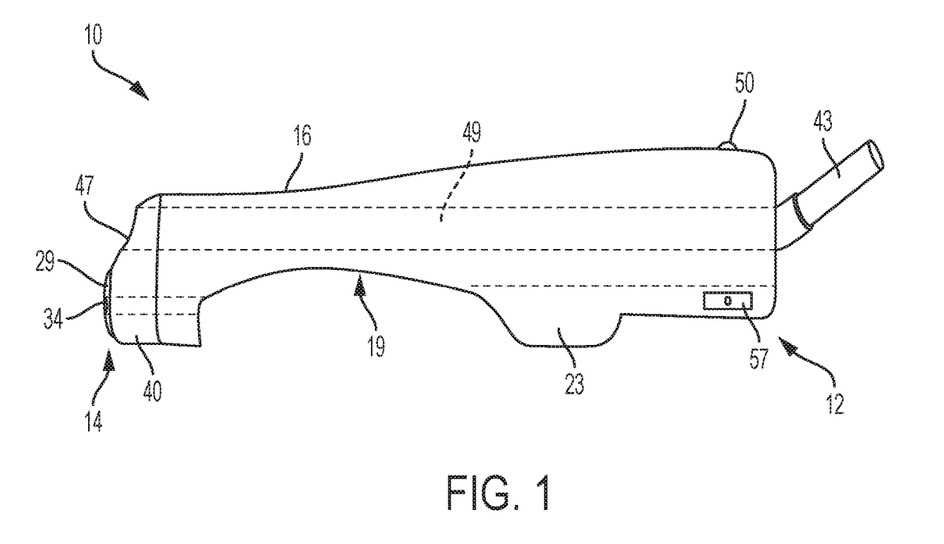
FIG. 1 shows a perspective view of one implementation of an illumination apparatus to be used in conjunction with an electrocautery pencil.

Turning now to FIG. 1, there is shown a side, perspective of an illumination device for use with an electrocautery pencil, generally indicated at 10. As will be discussed in additional detail below, the illumination device 10 may include a body 16 having a proximal end 12 and a distal end 14.

The body 16 of the illumination device 10 may include a mount 19, shaped to hold a universal-type electrocautery pencil body. The mount may define a space to hold any electrocautery pencil in place within the illumination device 10. The body 16 with the mount 19 may have with a standard shape which, in conjunction with an electrocautery pencil inserted into the mount 19, generally forms a handle for grasping by the surgeon. The body 16 may also have other shapes as desired for use with electrocautery devices. The body 16 may be shaped to have an ergonomic design, and may include, for example, a gripping surface to increase comfort and reduce slipping when used in wet conditions. The body 16 may also include other structures to help an electrocautery pencil to stay in place within the mount of the illumination device, such as projections 23, which may provide additional frictional contact with an electrocautery pencil.

By way of example, the mount 19 may be round, and may have a diameter of about 8 mm to about 20 mm, with 12 mm being a typical diameter, in order for standard electrocautery pencils to be inserted into the mount. The mount 19 may also be other various shapes and sizes, configured to accept different shapes and styles of electrocautery pencils. One having skill in the art would appreciate that many different designs exist for the shape of electrocautery pencils, and that the present disclosure could be configured to be compatible with any electrocautery pencil body design. The illumination device 10 may be constructed of any suitable material, such as injection molded plastic or other types of plastics, glass, silicon, etc.

Figure 2:
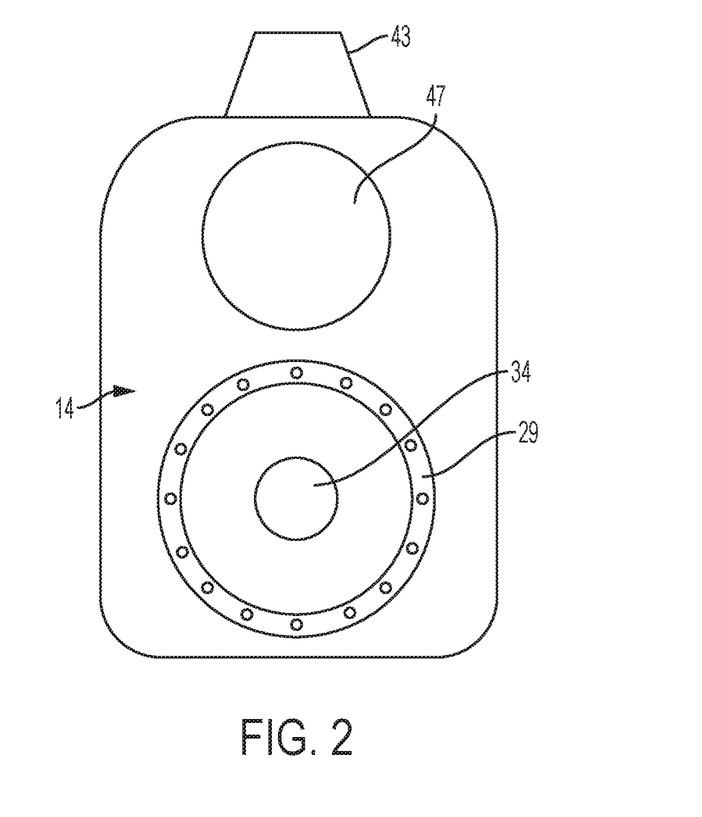
FIG. 2 shows a distal end view of the illumination apparatus of FIG. 1.

The distal end 14 of the illumination device may include a light source 29, and a void 34 for an electrocautery blade to pass there through. The void 34 may be round, and may have a diameter of about 2.4 mm (3/32 inches) to about 4.2 mm in order for standard electrocautery electrodes to be inserted through the void. The distal end 14 of the illumination device may include a portion that telescopes 40 (discussed in detail below) for use with cautery extenders. FIG. 2 shows a distal-end view of the illumination device of FIG. 1. The distal end 14 may include may include a light source 29 (for example, FIG. 2 shows a plurality of LEDs disposed circumferentially around void 34), a void 34 for receiving the blade end of an electrocautery pencil, and an opening 47 to receive smoke, gas, etc., from the surgical field. The mount may be round in shape, so as to be free from abrupt corners.

The light source may be comprised of light-emitting diodes, such as blue LEDS, white LEDs, yellow LEDs, etc. LEDs may be preferred in some implementations because they consume less energy, have a longer lifetime, are available in smaller sizes, emit less heat, and provide faster switching. Other types of lights may also be used, such as fluorescent, incandescent, etc. In addition to using a variety of types of lights, there are also numerous possibilities for the placement or configuration of the lights. For example, a single light may be used, or any number of lights may be used. As the light source is comprised of an increasing number of discrete lights, there may be a resulting enhanced illumination of the surgical field. Additionally, the implementation of lights spaced around the void 34 for an electrode tip virtually eliminates any shadow problems. It is appreciated that there are many various implementations for the light sources, and that the present disclosure encompasses an illumination device with a single light source, multiple light sources, and various implementations of light sources.

The proximal end 12 may include a connector 43 for connection to smoke evacuation tubing. Within the body 16, there may be provided a tube 49 for smoke evacuation (shown in dashed lines FIG. 1). The tube may include an opening 47 in the distal end 14 to receive smoke, a hollow portion between the distal end 14 and the proximal end 12, with the connector 43 at the proximal end 12 for connection to smoke evacuation tubing. Also within the body 16, there may be provided circuitry to electrically connect the light source 29 so that power (either from an external power source or from an internal battery) flows to the light source 29.

A switch 50 may be disposed on the body 16 to control the electrical supply to the light source 29. The light source 29 may be electrically connected to the electrocautery pencil (which may receive its power through the illumination device 10 from an external power supply). Thus, whenever the surgeon presses the switch 50, it may send power to the electrocautery pencil and the light source 29 will also receive power and become activated. The light source 29 may be electrically connected to the electrode through any means suitable and known in the art. In other implementations, the light source may be powered by a battery. The body 16 of the illumination device may be provided with a slot 57 to receive a battery, the battery in electrical connection to the light source. For example, the electrical connection may be by a folded wire that is housed in the device and unfolds as it is extended, or, for example, by electrical contacts that maintain a contact as the telescoping portion 40 telescopes outwardly.

The light source 29 may receive power from a battery, and the illuminating device may be provided with a slot 57 for such a battery. Depending on regulatory requirements, it may be desirable to have a slot 57 for a battery so that the battery may be removed and disposed of according to regulatory requirements. In other implementations, a battery may be integral to the illuminating device. A single battery may be used, or multiple batteries. Alternatively, the light source 29 may be configured to be electrically attached to the electrocautery device 20, as discussed above.

Figure 3:
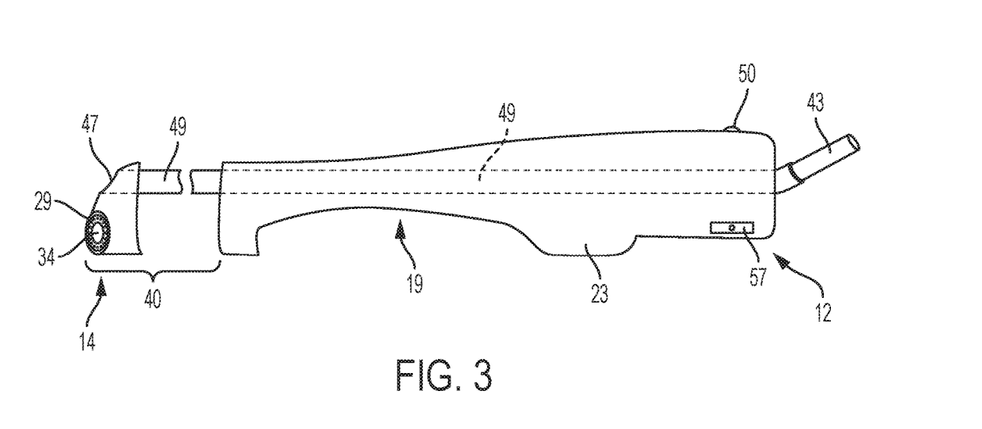
FIG. 3 shows a perspective view of the illumination apparatus of FIG. 1 with the telescoping end moved distally.

Turning now to FIG. 3, there is shown a perspective view of the illumination device of FIGS. 1 and 2 with the telescoping portion 40 of the distal end 14 telescoped outwardly. The telescoping portion 40 may be telescoped outwardly or inwardly depending on the surgical needs. For example, when an electrocautery extender is to be used, the telescoping portion 40 may be moved outwardly, such that the light source moves distally and is located near the surgical field. The tube 49 for smoke evacuation may also telescope with the distal end such that the smoke, etc., near the surgical field may be removed.

Figure 4:
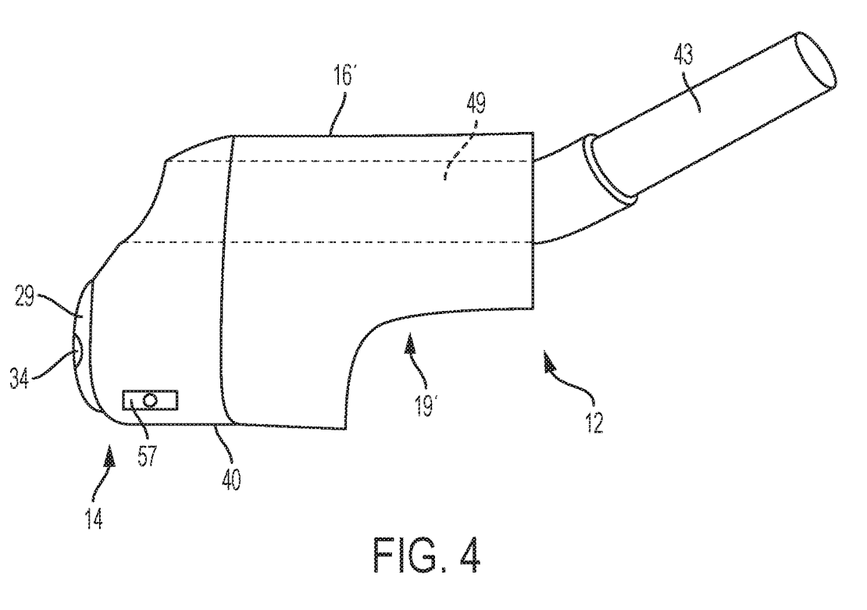
FIG. 4 shows a perspective view of another possible implementation of an illumination apparatus described herein.

Turning now to FIG. 4, there is shown an alternate configuration for the body 16' of the illumination device. It will be appreciated that the body may have many different shapes and sizes and still accomplish the purposes of the present disclosure. For example, the body 16' shown in FIG. 4 is somewhat truncated compared to the body shown in FIGS. 1 and 3. Various shapes may be provided depending on the intended use of the device. For example, the configuration shown in FIG. 4 may be useful with shorter cautery extenders, while the configuration shown in FIGS. 1 and 3 may be necessary when longer cautery extenders are to be used. FIG. 4 also illustrates that the battery slot 57 may be placed at different locations on the body of the illumination device, with the battery slot in electrical connection to the light source 29.

Figure 5:
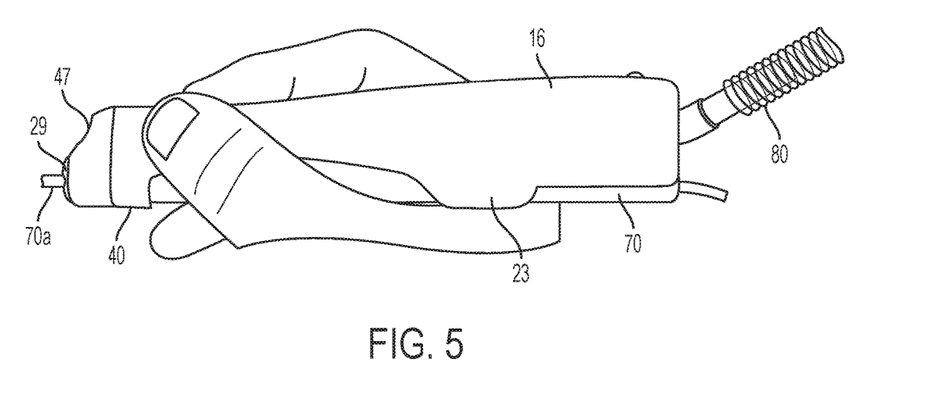
FIG. 5 shows a perspective view of an illumination apparatus with an electrocautery pencil inserted, as it may be used by a surgeon in practice.

In use, the surgeon may select an electrocautery pencil 70 (FIG. 5) with the appropriate tip 70a. The surgeon may then select an illumination device 10 with a light source 29 and smoke evacuation opening 47 disposed on the distal end 14. The tip 70a of the electrocautery pencil may be placed through void 34 in the body 16 of the illumination device, with the body of the electrocautery pencil 70 being inserted into mount 19. The projections 23 may assist in frictionally keeping the electrocautery pencil in place in the mount 19. Standard evacuation tubing 80 may be placed on the connector 43 for smoke evacuation. FIG. 5 shows an electrocautery pencil 70 in place in the illumination device, with a surgeon holding the device as it may be held in use for surgery. If desired, an electrocautery extender may be used, and the telescoping portion 40 may be moved distally to allow for the extender.

By placing the light source directly on the distal end of the illumination device, the surgeon may have better view of the treatment site and fewer persistent shadow problems. Additionally, surgeons need not purchase an entirely new electrocautery pencil to realize the advantages described herein. Surgeons need only to buy a new illumination device for use in their current electrocautery pencils, and do not need to replace an entire electrocautery pencil to have additional light. Furthermore, the illumination device can also replace any suction device that was previously needed and provide suction that is proximal to the surgical field without the need of additional instruments that may crowd the surgical field.

There is thus disclosed an improved lighting device and method for use in electrocautery pencils. It will be appreciated that numerous changes may be made to the present invention without departing from the scope of the claims.

What is claimed is:

1. An illuminating device for use with an electrocautery device comprising:
   a mounting portion connected to a telescoping portion, the mounting portion having a distal end and a proximal end, and a length extending therebetween;
   a mount disposed between the distal end and the proximal end of the mounting portion, the mount defining a space to receive a body of the electrocautery device, and the mount further comprising at least one projection for frictional contact with the body of the electrocautery device on a bottom side of the mount, the space to receive the body of the electrocautery device further comprising an opening to allow one or more controls on the body of the electrocautery device to be accessed when the body of the electrocautery device is located within the mount;
   the mounting portion further comprising a connector disposed on the proximal end, the connector attached to a proximal end of a hollow portion, the hollow portion located within the mounting portion and extending from the proximal end to the distal end of the mounting portion, the hollow portion being above the mount;
   the telescoping portion defining a void for an electrocautery blade of the electrocautery device to pass therethrough;
   the telescoping portion having a distal end and a proximal end, and a light source disposed on the distal end of the telescoping portion, the telescoping portion configured to telescope relative to the mounting portion from a first, retracted position wherein the proximal end of the telescoping portion abuts the distal end of the mounting portion, to a second, extended position wherein there is a space between the proximal end of the telescoping portion and the distal end of the mounting portion;
   the distal end of the telescoping portion further comprising a smoke evacuation void positioned above the void for the electrocautery blade of the electrocautery device, the smoke evacuation void connected to a tube for smoke evacuation, the tube for smoke evacuation passing through the hollow portion of the mounting portion, such that the telescoping portion comprising the void for the electrocautery blade of the electrocautery device telescopes relative to the electrocautery blade of the electrocautery device, and wherein the smoke evacuation void and the light source telescope together relative to the electrocautery blade.

2. The illuminating device of claim 1, wherein the light source is circular.

3. The illuminating device of claim 1, wherein the light source comprises multiple light emitting diodes.

4. The illuminating device of claim 3, wherein the multiple light emitting diodes are spaced circumferentially around the void of the distal end.

5. The illuminating device of claim 1, wherein the light source is in electrical connection to the electrocautery device.

6. The illuminating device of claim 1, further comprising a slot for a removable battery.

7. The illuminating device for use with an electrocautery device of claim 1, wherein the electrocautery blade of the electrocautery device passes through the void of the telescoping portion.

8. The illuminating device for use with an electrocautery device of claim 1, wherein the telescoping portion and the mounting portion are slidably attached by the tube for smoke evacuation passing through the hollow portion of the mounting portion.

9. An illumination device for illuminating a surgical field of an electrocautery pencil, the illumination device comprising:
   a sleeve with a distal end and a proximal end, the distal end comprising a telescoping portion, the telescoping portion having a distal end and a proximal end, a light source attached to the telescoping portion, and a void;
   wherein the sleeve defines a mounting portion comprising an open interior, the open interior defining a space below the void to receive at least a distal end of the electrocautery pencil, the open interior further configured to allow one or more controls on the electrocautery pencil to be accessed when the electrocautery pencil is within the open interior, wherein the mounting portion further comprises a distal end and a proximal end, the distal end of the mounting portion abutting the proximal end of the telescoping portion in a retracted position, and a hollow portion extending from the distal end of the mounting portion to the proximal end of the mounting portion; and wherein the distal end of the sleeve further comprises a tube for smoke evacuation connected to the void, and the proximal end of the sleeve comprises a connector for connection to smoke evacuation tubing, the distal end of the sleeve telescoping relative to the distal end of the electrocautery pencil.

10. The illumination device according to claim 9, wherein the open interior defines a space between the distal end and the proximal end to receive the electrocautery pencil.

11. The illumination device according to claim 9, wherein the sleeve further comprises a slot to receive a battery.

12. The illumination device according to claim 9, wherein the light source comprises multiple light-emitting diodes, and the multiple light emitting diodes spaced around the void.

13. An illumination device for illuminating a surgical field of an electrocautery pencil, the illumination device comprising:

a body comprising a mounting portion and a telescoping portion, the mounting portion comprising a mount defining a space to receive at least a distal end of the electrocautery pencil, the mounting portion further comprising a hollow therein, the hollow disposed above the space to receive at least a distal end of the electrocautery pencil, the mounting portion having a proximal end and a distal end, and the telescoping portion having a distal end and a proximal end;

the distal end of the telescoping portion comprising a first opening for smoke evacuation, a second opening for receiving a blade of the electrocautery pencil, the second opening disposed below the first opening for smoke evacuation, and a light source disposed thereon, wherein the telescoping portion is configured for telescoping relative to the mounting portion from a first, retracted position wherein the proximal end of the telescoping portion abuts the distal end of the mounting portion to a second, extended position;

and wherein the first opening for smoke evacuation and the light source telescope together relative to the blade of the electrocautery pencil.

14. The illumination device of claim 13, wherein the hollow comprises a hollow for smoke evacuation from the first opening of the distal end to the proximal end, and a connector attached to the proximal end for connection to smoke evacuation tubing.

15. The illumination device of claim 13, the second opening configured to allow an electrocautery blade to pass therethrough.

16. The illumination device of claim 13, the second opening configured to allow an electrocautery extender to pass therethrough.

17. The illumination device of claim 13, wherein the light source comprises two or more light-emitting diodes disposed circumferentially around the second opening.

18. The illumination device of claim 13, further comprising a slot to receive a removable battery.

19. The illumination device of claim 13, wherein the space of the mount is configured to allow access to one or more controls on the electrocautery pencil when the electrocautery pencil is located within the space of the mount.

20. The illumination device of claim 13, wherein the space of the mount further comprises one or more arcuate cut-outs into the mounting portion of the body to allow access to one or more controls on the electrocautery pencil when the electrocautery pencil is located within the space of the mount.

* * * * *